US007417138B2

(12) United States Patent
Kim et al.

(10) Patent No.: US 7,417,138 B2
(45) Date of Patent: Aug. 26, 2008

(54) PNA CHIP FOR DETERMINING GENOTYPES OF MYCOBACTERIAL SPECIES USING PLASTIC SUBSTRATE COATED WITH EPOXY GROUP-CONTAINING POLYMER AND METHOD OF DETERMINING GENOTYPES OF MYCOBACTERIAL SPECIES USING THE PNA CHIP

(75) Inventors: In Soo Kim, Daejeon (KR); Young Suk Park, Daejeon (KR); Gihune Jung, Seongnam (KR); Jinseok Kang, Suwon (KR)

(73) Assignee: LG Life Sciences, Ltd. (KR)

( * ) Notice: Subject to any disclaimer, the term of this patent is extended or adjusted under 35 U.S.C. 154(b) by 0 days.

(21) Appl. No.: 11/354,485

(22) Filed: Feb. 15, 2006

(65) Prior Publication Data

US 2006/0183148 A1 Aug. 17, 2006

(30) Foreign Application Priority Data

Feb. 16, 2005 (KR) ...................... 10-2005-0012893
Dec. 17, 2005 (KR) ...................... 10-2005-0124918

(51) Int. Cl.
*C07H 21/04* (2006.01)
*C07H 19/00* (2006.01)
*C07H 21/02* (2006.01)
*C12Q 1/68* (2006.01)

(52) U.S. Cl. ...................... 536/24.32; 435/6; 435/91.1; 435/91.2; 435/287.1; 536/22.1; 536/23.1; 536/23.7; 536/24.3; 536/24.31; 536/24.33

(58) Field of Classification Search ...................... 435/6, 435/91.1, 91.2, 287.1; 536/22.1, 23.1, 23.7, 536/24.3, 24.31, 24.32, 24.33
See application file for complete search history.

(56) References Cited

U.S. PATENT DOCUMENTS 6,670,130 B1 12/2003 Kim et al.
6,713,255 B1 3/2004 Makino et al.

FOREIGN PATENT DOCUMENTS

JP 2003161739 6/2003
KR 1020010084904 A 9/2001
KR 20020343606 B1 7/2003

OTHER PUBLICATIONS

Goodfellow, M., et al. "Circumsription of the Genus", in, The Mycobacteria, A Sourcebook, Part A, eds. Kubica and Wayne, Marcel Dekker, Inc., New York, 1984, pp. 1-24.*
Bevington, John C., "The Synthesis, Characterization, Reactions & Applications of Polymers," *Comprehensive Polymer Science* (1989) 3: 65-83.
Havlir, Diane and Barnes, Peter, "Tuberculosis In Patients With human Immunodeficiency Virus Infection," *New Journal of Medicine* (1999) 340(5): 367-373.

Jaworek, Thomas et al., "Radiation Curable Materials—Principles and New Perspectives," *Macromol. Symp.* (2000) 159: 197-204.
Shinnick, T.M. and Good, R.C., "Mycobacterial Taxonomy," *Eur.J. Clin. Microbiol. Infect. Dis.* (1994) 13(11): 884-901.
Tedder, John M., "Which Factors Determine the Reactivity and Regioselectivity of Free Radical Substitution and Addition Reactions?," *Agnew. Int. Ed. Engl.* (1982) 401-410.
American Thoracic Society, "Diagnosis and Treatment of Disease Caused by Nontuberculous Mycobacteria," Am J Respir Crit Care Med (1997) 156: S1-S25.
Hughes, Austin L., "Contrasting Evolutionary Rates in the Duplicate Chaperonin Genes of *Mycobacterium tuberculosis* and *M. Leprae*," *Mol. biol. Evol.* (1993) 10(6): 1343-1359.
Byrup, Birgitte and Nielsen, Peter E., "Peptide Nucleic Acids (PNA): Synthesis, Properties and Potential Applications," *Bioorganic & Medicinal Chemistry* (1996) 4(1): 5-23.
Kam, Kai Man et al., "Trends in Multidrug-Resistant *Mycobacterium tuberculosis* in Relation to Sputum Smear Positivity in Hong Kong, 1989-1999," *Clinical Infectious Disease* (2002) 34: 324-329.
Lee, Hyeyoung et al., "Species Identifications of Mycobacteria by PCR-Restriction Fragment Length Polymorphism of the *rpoB* Gene," *J. of Clin. Microbiol.* (2000) 3(8): 2966-2971.
Noordhoek, Gerda T, et al., "Sensitivity and Specificity of PCR for Detection of *Mycobacterium tuberculosis*: a Blind Comparison Study among Seven Laboratories," *J. of Clin. Microbiol.* (1994) 32(2): 277-284.
Wilson, Stuart M. et al., "Progress toward a simplified Polymerase Chain Reaction and Its Application to Diagnosis of *Tuberculosis*," *J. of Clin. Microbiol.* (1993) 31(4): 776-782.
Giordano, B.C. "Toward Dynamic Coating of Glass Microchip Chambers for Amplifying DNA Via Polymerase Chain Reaction," Electrophoresis (2001) 22: 334-340.
Priola, A. "UV Curable Coatings on Plastic Substrates: Dynamic Mechanical Thermal Analysis and Fourier Transformation Intra-Red Analysis of Interfacial Layer," Int. J. Adhesion and Adhesives (1991) 11(4): 255-259.
International Search Report for International Application No. PCT/KR2006/000382. Dated May 11, 2006.
Written Opinion of International Searching Authority for International Application No. PCT/KR2006/000382. Dated May 11, 2006.

* cited by examiner

*Primary Examiner*—Rodney P. Swartz
(74) *Attorney, Agent, or Firm*—Cantor Colburn LLP (57) ABSTRACT

Provided are a PNA chip for determining the genotypes of mycobacterial species in which probe PNAs having DNA sequences of SEQ ID NOs: 5-28 are immobilized on a plastic substrate coated with an epoxy group-containing polymer, and a method of determining the genotypes of mycobacterial species using the PNA chip. According to the PNA chip and the method of determining the genotypes of mycobacterial species, the genotypes of mycobacterial species which are causes of tuberculosis and respiratory diseases can be determined within a short term with good sensitivity and specificity. Therefore, detection of the presence of mycobacterial species in test samples, and after confirmation of the presence of mycobacterial species, identification of the mycobacterial species and determination of whether or not the mycobacterial species are tuberculosis-causing mycobacterial species can be achieved promptly and accurately.

13 Claims, 4 Drawing Sheets

| | |
|---|---|
| ⓟ ⓟ ⓜ ⓝ ⓝ | |
| ① ① ⑫ ⑫ | |
| ② ② ⑬ ⑬ | |
| ③ ③ ⑭ ⑭ | |
| ④ ④ ⓜ ⑮ ⑮ | |
| ⑤ ⑤ ⑯ ⑯ | |
| ⑥ ⑥ ⑰ ⑰ | |
| ⑦ ⑦ ⑱ ⑱ | ⓟ POSITIVE CONTROL |
| ⑧ ⑧ ⓜ ⑲ ⑲ | ⓝ NEGATIVE CONTROL |
| ⑨ ⑨ ⑳ ⑳ | ⓜ POSITION MARKER |
| ⑩ ⑩ ㉑ ㉑ | ① - ㉒ SPECIES-SPECIFIC PROBES |
| ⑪ ⑪ ㉒ ㉒ | |
| ⓝ ⓝ ⓜ ⓟ ⓟ | |

PNA CHIP FOR DETERMINING GENOTYPES OF MYCOBACTERIAL SPECIES USING PLASTIC SUBSTRATE COATED WITH EPOXY GROUP-CONTAINING POLYMER AND METHOD OF DETERMINING GENOTYPES OF MYCOBACTERIAL SPECIES USING THE PNA CHIP

CROSS-REFERENCE TO RELATED PATENT APPLICATION

This application claims priority from Korean Patent Application Nos. 10-2005-0012893, filed on Feb. 16, 2005 and 10-2005-0124918, filed on Dec. 17, 2005, in the Korean Intellectual Property Office, the disclosure of which is incorporated herein in its entirety by reference.

1. Field of the Invention

The present invention relates to a peptide nucleic acid (PNA) chip for determining the genotypes of mycobacterial species using a plastic substrate coated with an epoxy group-containing polymer and a method of determining the genotypes of mycobacterial species using the same. More particularly, the present invention relates to a PNA chip for determining the genotypes of mycobacterial species in which probe PNAs having DNA sequences of SEQ ID NOs: 5-28 are immobilized on a plastic substrate coated with an epoxy group-containing polymer, and a method of determining the genotypes of mycobacterial species using the PNA chip.

2. Description of the Related Art

Tuberculosis is a leading infectious disease of death throughout human history and is caused by tuberculosis-causing bacteria belonging to the genus *Mycobacteria* which are rod-shaped, 0.2-0.5 μm thick, and 1-4 μm long. Many members of the genus *Mycobacteria* cause a respiratory disease such as tuberculosis, Hansen's disease, etc. in humans and animals, and more than 100 mycobacterial species have been identified to date (Shinnick T M and Good R C., Mycobacterial taxonomy. Eur J Clin Microbiol Infect Dis. 1994;13 (11):884-901). *Mycobacterium tuberculosis* is known as a major bacterial strain causing tuberculosis in humans. Rare cases of human tuberculosis are caused by *Mycobacterium bovis*. It is known that *Mycobacterium leprae* causes Hansen's disease (Hughes A L. Contrasting evolutionary rates in the duplicate chaperonin genes of *Mycobacterium tuberculosis* and *M. leprae*. Mol Biol Evol. 1993; 10(6):1343-59).

Meanwhile, there exist nontuberculous *mycobacteria* (NTM) which generally do not cause tuberculosis in normal persons but cause atypical tuberculosis in patients with acquired immunodeficiency syndrome (AIDS) and other immunodeficiency syndrome. Examples of NTM include *M. avium-intracellulare* complex (*M. avium* complex), *M. fortuitum, M. chelonae, M. gordonae, M. szulgai, M. kansasii, M. africanum,* and *M. genavense* (Barnes P F et al., Tuberculosis in patients with human immunodeficiency virus infection. N Engl J Med. 1991;324(23):1644-1650).

Tuberculosis caused by infection with the above-illustrated bacterial strains is one of diseases that occur in economically underdeveloped countries. Every year, 120,000 people are infected with tuberculosis bacteria in Korea. During 2003, a total of 30,687 new tuberculosis cases (64 cases per 100,000 population) were reported in Korea. According to a data announced by the bureau of Statistics in 2004, Korea had the highest death rate associated with tuberculosis infection among the 30 countries in the Organization for Economic Development and Cooperation (OECD).

Recently, it is increasingly reported that AIDS or other immunodeficient patients or less immunocompetent infants, when infected with NTM, show clinical symptoms similar to those observed in patients with tuberculosis infection. Many NTM have a multidrug resistance to anti-tuberculosis drugs, which makes it difficult to treat tuberculosis (Kam K M et al., Trends in Multidrug-Resistant *Mycobacterium tuberculosis* in Relation to Sputum Smear Positivity in Hong Kong, 1989-1999. Clin Infect Dis. 2002;34(3):324-329).

Thus, to individually appropriately treat patients infected with tuberculosis or nontuberculosis *mycobacteria,* early detection and diagnosis of patients infected with tuberculosis or nontuberculosis *mycobacteria* are essentially needed.

The diagnosis of tuberculosis in patients is generally made by clinical symptoms, tuberculin skin test, X-ray photography, bacteriological test, etc. The tuberculin skin test is the simplest means for identifying patients infected with tuberculosis, but often produces a false-negative result during anergy due to serious tuberculosis, measles, and immunosuppression. The efficacy of the X-ray photography is determined by the reader's ability and average 25% of patients diagnosed positive by X-ray examination are demonstrated negative by other diagnostic test. Thus, the diagnosis of tuberculosis by X-ray photography depends on the finding of abnormal opacities and accurate interpretation of the abnormal opacities by the reader. The bacteriological test is a reliable method for diagnosing tuberculosis infection, and includes a smear examination, a culture test, a molecular diagnostic test, etc.

The smear examination generally utilizes Ziehl-Neelsen acid-fast staining. Although it is a simple and rapid diagnostic technique, identification of tuberculosis and nontuberculosis *mycobacteria* is difficult and detection sensitivity is also low.

With respect to the culture test, the detection sensitivity is very high such that the detection of tuberculosis bacteria is possible even when only 10 bacteria are contained in 1 ml of a test sample. Furthermore, since tuberculosis *mycobacteria* can be isolated, accurate diagnosis can be made. However, the culture test requires a long-term culture for about 4-8 weeks and an observation by skilled persons to get the test results, and thus, it is not suitable for the treatment of tuberculosis patients. A BACTEC method (Becton Dickinson, America) is a novel method for diagnosis of tuberculosis that radioisotopically measures the amount of $^{14}CO_2$ produced by the metabolism of bacteria inoculated onto a liquid medium containing $C^{14}$-palmitate and expresses the measured amount of $^{14}CO_2$ as the growth level. This method takes average 16 days to get the results. However, there is a problem that facilities and skilled persons for safe handling and management of radioisotopes are required.

A polymerase chain reaction (PCR) test is a method of rapidly and accurately diagnosing tuberculosis by amplification of specific gene sites within 2-3 hours. The PCR test is a useful technique enabling the diagnosis of tuberculosis in clinical samples with sensitivity and specificity of 95% or more within one day (Wilson S M et al., Progress toward a simplified polymerase chain reaction and its application to diagnosis of tuberculosis. J Clin Microbiol. 1993; 31(4):776-78). However, carry-over contamination is likely to occur, and highly skilled persons who can perform the PCR test are needed (Noordhoek G T et al., Sensitivity and specificity of PCR for detection of *Mycobacterium tuberculosis:* a blind comparison study among seven laboratories. J Clin Microbiol. 1994;32(2):277-284).

Recently, NTM infection in immunodeficient patients or less immunocompetent infants increases the incidence of atypical tuberculosis. The symptoms of atypical tuberculosis are very similar to those of typical tuberculosis, but drugs different from those used for the treatment of typical tuberculosis may be indicated to treat the atypical tuberculosis. Thus, it is essential to accurately identify bacterial species that cause tuberculosis or tuberculosis-like infections. In particular, it is known that primary antituberculosis drug susceptibility of *M. avium-intracellulare* complex (MAC), which is the most common species of NTM, is 10 to 100-fold lower than that of tuberculosis bacteria. Thus, the American Thoracic Society provides a guideline about diagnosis and treatment of diseases caused by NTM (American Thoracic Society, Diagnosis and treatment of disease caused by nontuberculous *mycobacteria*. Am J Respir Crit Care Med. 1997;156(2):S1-S25).

As molecular biological techniques for identification of mycobacterial species, there are currently commonly used polymerase chain reaction-restriction fragment length polymorphism (PCR-RFLP) using restriction enzymes and PCR-hybridization using specific probes. PCR-RFLP provides simple and rapid results after PCR amplification but is difficult to apply in determination of various genotypes. Further, when restriction enzymes fail to recognize specific sequence sites, inaccurate analysis results may be obtained (Lee H et al., Species identification of *mycobacteria* by PCR-restriction fragment length polymorphism of the rpoB gene. J Clin Microbiol. 2000;38(8):2966-71). INNO-LiPA *MYCOBACTERIA* v2 (www.innogenetics.com, Innogenetics, Belgium) is a commercially available assay method of PCR-hybridization. According to this assay method, probes complementary to the nucleotide sequences of genetic polymorphism sites are synthesized, and diagnosis is established based on the hybridization of the probes with PCR products. The use of various types of probes guarantees accurate assay results, but only a limited number of probes can be spotted due to the use of filters. Also, since only one type of *mycobacteria* is detected using one filter, the assay of a large number of test samples requires considerable time and skilled persons.

A DNA microarray (DNA chip) kit for determining the genotypes of mycobacterial species was recently developed (Korean Patent No. 10-0343606). The response of PCR products on a glass slide on which various species-specific DNA probes are immobilized is analyzed by a microarray scanner. The DNA microarray kit enables a simultaneous assay of two samples on one glass slide using a scanner, and thus can offer more objective, numerical results, as compared with the INNO-LiPA *MYCOBACTERIA* v2 commercially available from Innogenetics. However, the DNA probes used in the microarray kit easily react with water molecules in air, and due to biological and chemical instability of DNA bases, the performance and reactivity of DNAs may be lowered as the storage duration is longer. Furthermore, the use of a glass slide and a cover glass easily causes a crack formation in the glass and thus increases the risk of accidents. The structural change of the DNA microarray kit for convenience of use is also difficult.

Therefore, while searching for a solution to the above problems, the present inventors found that detection of the presence of mycobacterial species in test samples, and after confirmation of the presence of mycobacterial species, identification of the mycobacterial species and determination of whether or not the mycobacterial species were tuberculosis-causing mycobacterial species could be achieved promptly and accurately through the determination of the genotypes of mycobacterial species on a peptide nucleic acid (PNA) chip in which mycobacterial species-specific probe PNAs were immobilized on a plastic substrate coated with an epoxy group-containing polymer, and thus, completed the present invention.

SUMMARY OF THE INVENTION

According to an aspect of the present invention, there is provided a peptide nucleic acid (PNA) chip for determining the genotypes of mycobacterial species wherein probe PNAs having DNA sequences of SEQ ID NOs: 5-28 are immobilized on a plastic substrate coated with an epoxy group-containing polymer.

The plastic substrate may be a transparent plastic substrate made of a material selected from the group consisting of polymethylmethacrylate (PMMA), polycarbonate (PC), polynorbonene, cyclic olefin copolymer (COC), fluorinated polyimide, polystyrene (PS), styrene-butadiene copolymer (SBC), acrylonitrile butadiene styrene (ABS), styrene acrylonitrile (SAN), and polysulfone.

The epoxy group-containing polymer may be a copolymer of an epoxy group-containing acrylate monomer and an epoxy group-free acrylate monomer.

The epoxy group-containing polymer may be a copolymer of an epoxy group-containing acrylate monomer and a highly viscous acrylate monomer, as represented by Formula 1 below:

wherein $R^1$ is an epoxy-containing ester, $R^3$ is hydrogen or an alkyl group, and X is a highly viscous acrylate compound.

The highly viscous acrylate monomer may be selected from the group consisting of dipentaerythrithol hydroxy pentaacrylate (DPHA), 9-ethyleneglycol diacrylate (9-EGDA), pentaerythritol tri,tetraacrylate (PETA), polyethyleneglycol 400 diacrylate, tripropyleneglycol diacrylate, trimethylol propane triacrylate, and dipentaerythritol hexacrylate.

The epoxy group-containing polymer may be a copolymer of an epoxy group-containing acrylate monomer and an acrylate derivative capable of adhering to the plastic substrate, as represented by Formula 2 below:

wherein $R^1$ is an epoxy-containing ester, $R^2$ is an alkylester, and $R^3$ is hydrogen or an alkyl group.

The acrylate derivative capable of adhering to the plastic substrate may be selected from the group consisting of methylmethacrylate (MMA), ethylacrylate, ethylmethacrylate (EMA), n-propylacrylate, n-propylmethacrylate, isopropylacrylate, and isopropylmethacrylate.

The content of the epoxy group in the epoxy group-containing polymer may be 20~30%.

The PNA chip may further comprise an ether-containing or ether-free carboxylic acid linker of 5-8 carbon atoms with an amino functional group that is connected to amino terminals of the probe PNAs.

According to another aspect of the present invention, there is provided a method of determining the genotypes of mycobacterial species, the method including: a) applying a reaction sample containing target DNAs to the PNA chip of the present invention; b) hybridizing the target DNAs with the probe PNAs; c) washing the PNA chip to remove a nonspecific reaction product; and d) detecting a fluorescent signal emitted from the resultant PNA/DNA hybrids.

The target DNAs may be obtained by PCR amplification using primers having DNA sequences of SEQ ID NOs: 1-4.

The primers may be biotin- or rhodamine-labeled primers.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

The present invention provides a peptide nucleic acid (PNA) chip for determining the genotypes of mycobacterial species in which probe PNAs having DNA sequences of SEQ ID NOs: 5-28 are immobilized on a plastic substrate coated with an epoxy group-containing polymer.

Figure 2:
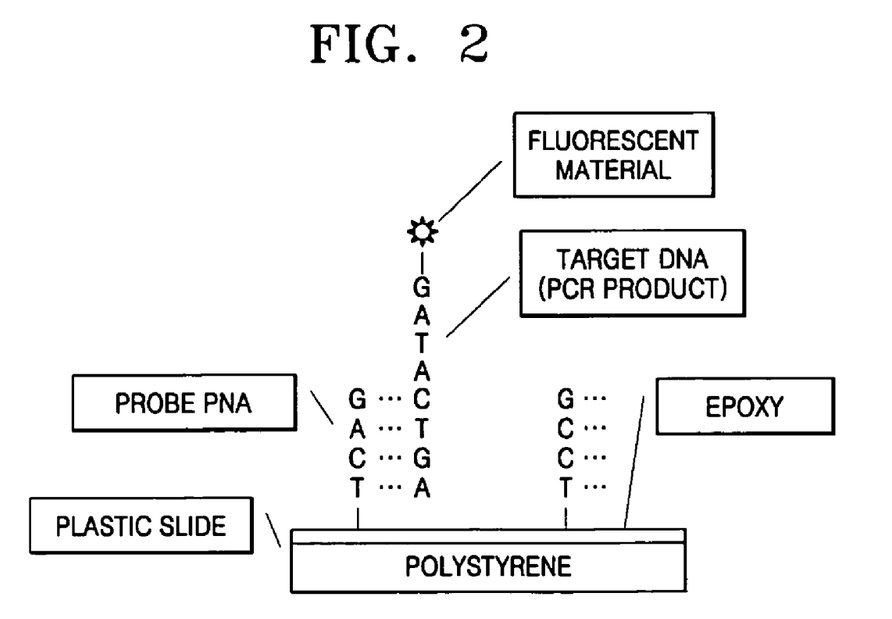
FIG. 2 is a sectional diagram illustrating a PNA chip according to the present invention.

FIG. 2 is a sectional diagram illustrating a PNA chip according to the present invention.

A substrate used for the PNA chip according to the present invention is a plastic substrate, preferably a transparent plastic substrate, instead of common silicon wafer and glass substrate. Conventionally, well-processed, expensive glass is mainly used as a material for a chip substrate. However, an inexpensive, easy-to-handle, common plastic substrate is used herein to overcome the disadvantages of a glass substrate. Generally, the transparent plastic substrate may be made of polymethylmethacrylate (PMMA), polycarbonate (PC), polynorbonene, cyclic olefin copolymer (COC), fluorinated polyimide, polystyrene (PS), styrene-butadiene copolymer (SBC), acrylonitrile butadiene styrene (ABS), styrene acrylonitrile (SAN), or polysulfone.

The epoxy group-containing polymer used for the PNA chip according to the present invention may be a copolymer of an epoxy group-containing acrylate monomer and a highly viscous acrylate monomer, as represented by Formula 1 below:

(1)

wherein $R^1$ is an epoxy-containing ester of $C_{3-12}$, $R^3$ is hydrogen or an alkyl group of $C_{1-16}$, X is a highly viscous acrylate compound, and n is 10 to 2,000.

The highly viscous acrylate monomer may be selected from the group consisting of dipentaerythrithol hydroxy pentaacrylate (DPHA), 9-ethyleneglycol diacrylate (9-EGDA), pentaerythritol tri,tetraacrylate (PETA), polyethyleneglycol 400 diacrylate, tripropyleneglycol diacrylate, trimethylol propane triacrylate, and dipentaerythritol hexacrylate.

The epoxy group-containing polymer used for the PNA chip according to the present invention may also be a copolymer of an epoxy group-containing acrylate monomer and an acrylate derivative capable of adhering to the plastic substrate, as represented by Formula 2 below:

(2)

wherein $R^1$ is an epoxy-containing ester of $C_{3-12}$, $R^2$ is an alkylester of $C_{2-16}$, $R^3$ is hydrogen or an alkyl group of $C_{1-16}$, and n is 10 to 2,000.

The acrylate derivative capable of adhering to the plastic substrate may be selected from the group consisting of methylmethacrylate (MMA), ethylacrylate, ethylmethacrylate (EMA), n-propylacrylate, n-propylmethacrylate, isopropylacrylate, and isopropylmethacrylate.

The epoxy group-containing polymer can be synthesized by a known polymerization method such as UV curing (see T. Jaworek, *Macromol Symp.*, 159, 197, 2000; Cliff Roffey, 'Photogeneration of Reactive Species for UV Curing', 1997) or radical polymerization (see Bevington, J. C., in '*Comprehensive Polymer Science*', Vol 3, 65 1989; Tedder, J. M., *Angew. Chem., Int. Ed. Engl.*, 21, 401, 1982) using acrylate-based compounds.

In synthesis of the epoxy group-containing polymer, the weight ratio of the epoxy group-containing acrylate monomer to the other acrylate monomer may be 0.1:99.9 to 100:0. The content of the epoxy group-containing acrylate monomer binding with a biomolecule may be 10 wt % or more. The content of the epoxy group in the epoxy group-containing polymer may be 20–30%. The reaction temperature may be 90° C. or less to prevent the ring-opening of the epoxy group.

The epoxy group-containing polymer may be coated on the plastic substrate using a method commonly known in the art, such as dipping, spraying, and printing.

The probe PNAs used in the PNA chip of the present invention have DNA sequences of SEQ ID NOs: 5-28. The DNA sequence of SEQ ID NO: 5 is a probe sequence that hybridizes with all species of *mycobacteria* (positive control), the DNA sequence of SEQ ID NO: 6 is a probe sequence that does not hybridize with any species of *mycobacteria* (negative control), and the DNA sequences of SEQ ID NOs: 7-28 are species-specific probe sequences based on the internal transcribed spacer (ITS) regions of *mycobacteria* which specifically hybridize with individual species of *mycobacteria*.

Figure 1:
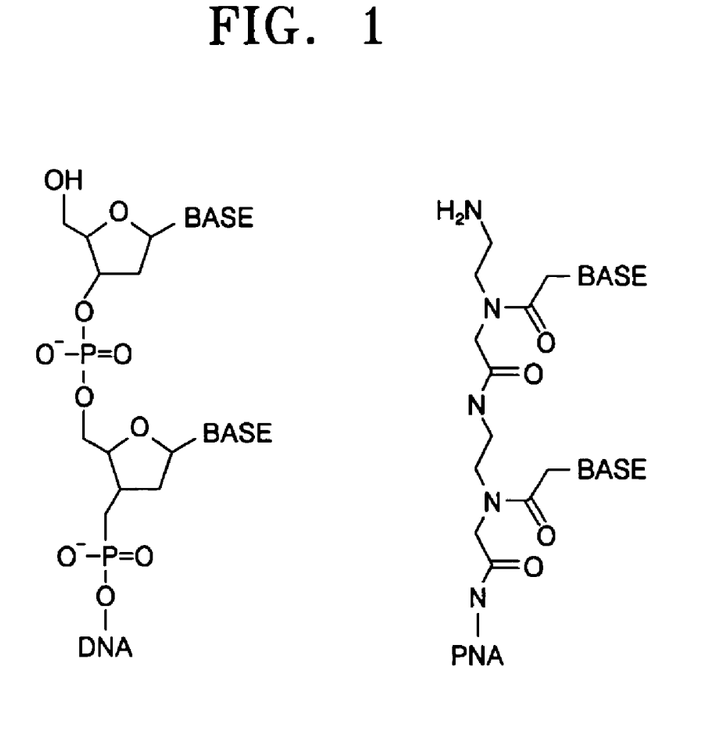
FIG. 1 illustrates a fundamental structural difference between DNA and PNA.

Generally, PNA, which was first developed in 1991, is an oligonucleotide analogue consisting of a peptide backbone composed of N-(2-aminoethyl)glycine units, unlike DNA consisting of a deoxyribose phosphate backbone, as shown in FIG. 1. A PNA-DNA duplex has higher specificity and binding strength than a DNA-DNA duplex and is stable biologically and chemically (Hyrup B and Nielsen P E, Peptide nucleic acids (PNA): synthesis, properties and potential applications. Bioorg Med Chem. 1996;4(1):5-23).

The immobilization of the probe PNAs on the plastic substrate coated with the epoxy group-containing polymer can be performed using a common DNA immobilization technique, e.g., spotting, microarraying, photolithography, or electronic addressing. Spotting is a technique of selectively dropping biomolecules onto desired sites with spatial movement of a microrobot, microarraying uses a fountain pen-like pin, and photolithography uses light to modify the surfaces of specific sites by illumination so that biomolecules bind with only the modified surfaces of the specific sites. Electronic addressing permits biomolecules to be directed and fixed to specific electrodes of a microelectrode array by adjusting the electrode voltage of the microelectrode array.

The PNA chip of the present invention may further comprise an ether-containing or ether-free carboxylic acid linker of 5-8 carbon atoms with an amino functional group that is connected to amino terminals of the probe PNAs.

Figure 4:
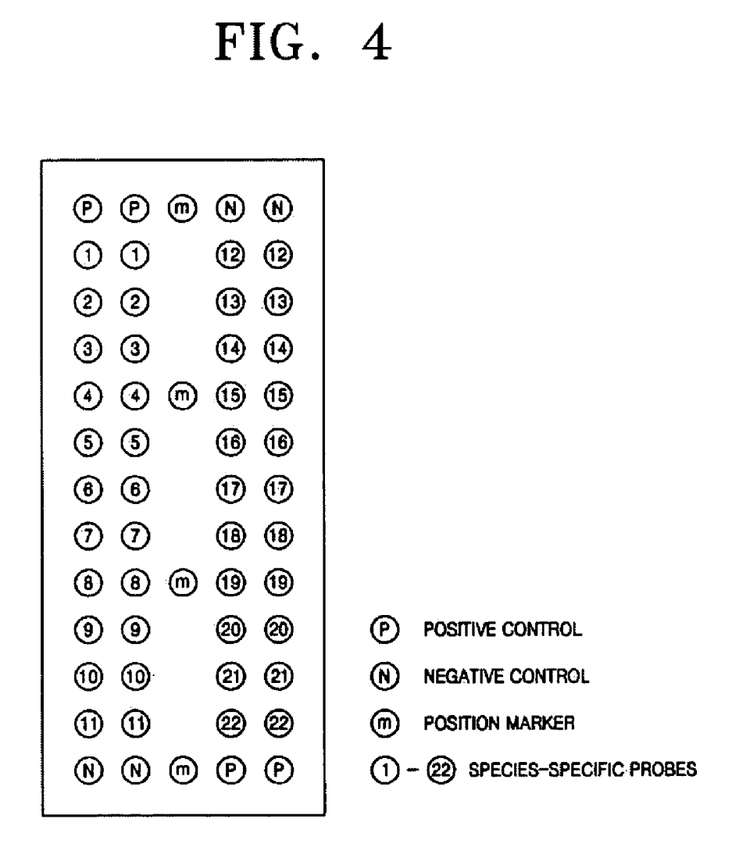
FIG. 4 illustrates an example of a probe array of a PNA chip for determining the genotypes of mycobacterial species in which probe PNAs are immobilized on a plastic substrate coated with an epoxy group-containing polymer according to the present invention.

FIG. 4 illustrates an example of a probe array of a PNA chip for determining the genotypes of mycobacterial species in which probe PNAs are immobilized on a plastic substrate coated with an epoxy group-containing polymer according to the present invention.

The present invention also provides a method of determining the genotypes of mycobacterial species using the PNA chip of the present invention.

The method of determining the genotypes of mycrobacterial species of the present invention includes a) applying a reaction sample containing target DNAs to the PNA chip of the present invention, b) hybridizing the target DNAs with the probe PNAs, c) washing the PNA chip to remove a nonspecific reaction product, and d) detecting a fluorescent signal emitted from the resultant PNA/DNA hybrids.

In the method of the present invention, the target DNAs may be obtained by amplifying template DNAs derived from sputum, body fluids, and urine of patients suspected of *mycobacteria* infection by PCR using primers having DNA sequences of SEQ ID NOs: 1-4.

In the method of the present invention, the primers may be biotin- or rhodamine-labeled primers.

According to the method of the present invention, the genotypes of mycobacterial species which are causes of tuberculosis and respiratory diseases can be determined within a short term with good sensitivity and specificity. Therefore, detection of the presence of mycobacterial species in test samples, and after confirmation of the presence of mycobacterial species, identification of the mycobacterial species and determination of whether or not the mycobacterial species are tuberculosis-causing mycobacterial species can be achieved promptly and accurately. When the identification of mycobacterial species is completed, the treatment regimens can be determined accordingly. In addition, the method of the present invention is expected to be effectively used in clinical and epidemiological diagnosis of infectious patients, tracking of infection pathway, establishment of monitoring systems for supervising tuberculosis bacteria, prediction of treatment response, development of therapeutic agents such as vaccines, etc.

Hereinafter, the present invention will be described more specifically with reference to the following Examples. The following Examples are for illustrative purposes and are not intended to limit the scope of the invention.

EXAMPLE 1

Synthesis of Primers for Preparation of Target DNAs

To prepare target DNAs, PCR primers were first synthesized. For this, nucleotide sequences capable of commonly reacting with 16S rDNAs, ITS regions, and 23S rDNAs of 25 mycobacterial species presented in Table 1 below were analyzed, and selected as PCR primers as presented in Table 2 below.

To detect hybridization products, rhodamine or biotin was added to 5'-ends of the PCR primers so that it was coupled with streptavidin-cyanine 3 after hybridization. In this Example, primers were synthesized on request by Metabion (Germany) according to the oligonucleotide synthesis method disclosed in 10.42 of Sambrook and Russell, Molecular cloning $3^{rd}$, Cold Spring Harbor Laboratory Press, New York, USA, 2001.

TABLE 1

| No. | Mycobacterial species (accession no.) |
|---|---|
| 1 | M. avium (ATCC 25291) |
| 2 | M. bovis (ATCC 19210) |
| 3 | M. chelonae (ATCC 35749) |
| 4 | M. fortuitum (ATCC 6841) |
| 5 | M. gastri (ATCC 15754) |
| 6 | M. gordonae (ATCC 14470) |
| 7 | M. intracellulare (ATCC 13950) |
| 8 | M. kansasii (ATCC 12478) |
| 9 | M. malmoense (ATCC 29571) |
| 10 | M. microti (ATCC 19422) |
| 11 | M. scrofulaceum (ATCC 19981) |
| 12 | M. simiae (ATCC 25275) |
| 13 | M. smegmatis (ATCC 19420) |
| 14 | M. terrae (ATCC 15755) |
| 15 | M. tuberculosis H37Rv (ATCC 27294) |
| 16 | M. tuberculosis (ATCC 35804) |
| 17 | M. vaccae (ATCC 15483) |
| 18 | M. africanum (ATCC 25420) |
| 19 | M. genavense (ATCC 51233) |
| 20 | M. marinum (ATCC 927) |
| 21 | M. xenopi (ATCC 19250) |
| 22 | M. szulgai (ATCC 35799) |
| 23 | M. flavescens (ATCC 14474) |
| 24 | M. lentiflavum (ATCC 51985) |
| 25 | M. abscessus (ATCC 19977) |

TABLE 2

| | | Primer sequence (5' → 3') | Remark |
|---|---|---|---|
| Primary PCR | Sense (SEQ ID NO: 1) | CCC GAA GCC RGT GGC CTA ACC | R = G + A |
| | Antisense (SEQ ID NO: 2) | CCA AGG CAT CCA CCA TGC GCC C | |
| Secondary PCR | Sense (SEQ ID NO: 3) | CTT TCT AAG GAG CAC CA | When the amount of primary PCR products was insufficient |
| | Antisense (SEQ ID NO: 4) | GAT GCT CGC AAC CAC TA | |

EXAMPLE 2

Preparation of Target DNAs Using PCR 1) 2-5 ml of sputum of each patient suspected of tuberculosis and an equal amount of 4N NaOH were placed in a 15 ml tube, sufficiently stirred, and centrifuged at 4,000 rpm for 20 minutes. The supernatant was discarded, and 10 ml of a PBS buffer (137 mM NaCl, 2.7 mM KCl, 10 mM $Na_2HPO_4$, 2 mM $KH_2PO_4$) was added to the precipitate, the resultant solution was thoroughly stirred and centrifuged at 4,000 rpm for 20 minutes. The supernatant was again discarded. The precipitate was transferred to a 1.5 ml tube and 1 ml of a PBS buffer was added thereto. The resultant solution was stirred and centrifuged at 13,000 rpm for 5 minutes. The supernatant was again discarded. 50-100 μl of 5% (w/v) Chelex 100 resin (Bio-Rad) was added to the precipitate, the resultant solution was heated at 100° C. for 20 minutes and centrifuged at 13,000 rpm for 3 minutes. DNAs were separated from the supernatant and used as template DNAs for PCR amplification.

2) A PCR composition was prepared according to the composition ratio presented in Table 3 below, and PCR was performed using a PTC200 thermal cycler (MJ Research, America).

Figure 3:
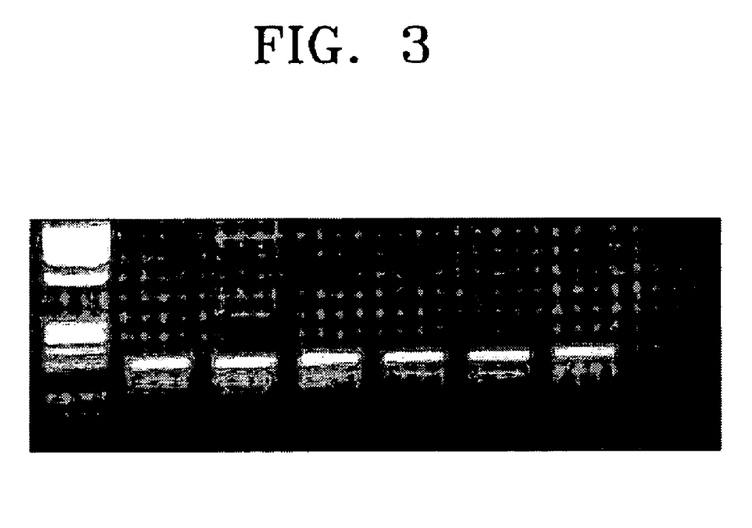
FIG. 3 is an electrophoretic image showing DNAs amplified by polymerase chain reaction (PCR) using the genus *Mycobacterium*-specific primers.

3) 1 µl of a gel loading buffer (0.25% bromophenol blue, 0.25% xylene cyanol FF, 15% Ficoll 400) was added to 5 µl of the PCR products, followed by electrophoresis on 1 µg/ml ethidium bromide (EtBr)-containing 2% agarose gel. PCR bands were detected using a UV transilluminator-attached image analyzer (Bio Rad, America). The results are shown in FIG. 3.

4) When the amount of the PCR products was insufficient, secondary PCR was performed using 2 µl of the primary PCR products as templates under the PCR conditions presented in Table 4 below, and the results of the secondary PCR were analyzed in the same manner as in 3).

TABLE 3

| Primary PCR composition | | PCR temperature profile | |
| --- | --- | --- | --- |
| Sterilized distilled water | 10.0 µl | 95° C., 5.0 min | 1 cycle |
| 10× buffer | 2.0 µl | | |
| 2 mM dNTPs | 1.0 µl | 94° C., 1.0 min | 35 cycles |
| 2~10 pmol primary sense primer | 1.0 µl | 60° C., 1.0 min | |
| 2~10 pmol primary antisense primer | 1.0 µl | 72° C., 1.0 min | |
| 1U Taq | 0.5 µl | | |
| DMA extracts | 4.5 µl | | |
| Total | 20 µl | 72° C., 5.0 min | 1 cycle |

TABLE 4

| Secondary PCR composition | | PCR temperature profile | |
| --- | --- | --- | --- |
| Sterilized distilled water | 12.5 µl | 95° C., 5.0 min | 1 cycle |
| 10× buffer | 2.0 µl | | |
| 2 mM dNTPs | 1.0 µl | 94° C., 0.5 min | 30 cycles |
| 2~10 pmol secondary sense primer | 1.0 µl | 62° C., 0.5 min | |
| 2~10 pmol secondary antisense primer | 1.0 µl | 72° C., 1.0 min | |
| 1U Taq | 0.5 µl | | |
| Primary PCR products | 2.0 µl | | |
| Total | 20 µl | 72° C., 5.0 min | 1 cycle |

EXAMPLE 3

Preparation of Probe PNAs

As presented in Table 5 below, genus-specific PNA probe hybridizing with all mycobacterial species, non-specific PNA probe hybridizing with no mycobacterial species, and 22 species-specific PNA probes hybridizing with only target species of *mycobacteria* were selected by analyzing the nucleotide sequences of the ITS regions of the 25 mycobacterial species listed in Table 2. For this, linkers were added to 5'-ends of PNAs, and 11-18 bp-long PNA probes were synthesized at about 58-62° C. considering Tm and GC % on an immobilized phase using an amino functional group-containing resin support and a cyclic Bts monomer, followed by cleavage from the resin, deprotection, HPLC purification, and analysis by MALDI-MS.

TABLE 5

| Probe name (SEQ ID NO:) | Nucleotide sequence* | Target genotype |
| --- | --- | --- |
| Myco 01 (5) | AAA CAC CAC ACC CC | Hybridization with all mycobacterial species (positive control) |
| Myco 02 (6) | AAA CAC TGG ACC CC | No hybridization with mycobacterial species (negative control) |
| Myco 03 (7) | CAC CTG GAA CAA GT | M. tuberculosis complex |
| Myco 04 (8) | GAC CGA GTG TTG TCT | MAC complex |
| Myco 05 (9) | CAC CCG CAA CCG | M. fortuitum |
| Myco 06 (10) | AGC GAG TAA CCA CT | M. chelonae |
| Myco 07 (11) | CCA CTA CAG ATG CCT A | M. abscessus |
| Myco 08 (12) | CAC TTG TTG GGA TGC | M. kansasii |
| Myco 09 (13) | GAC AGC ACC CGA | M. gordonae |
| Myco 10 (14) | ACC ACT CAG AAC GA | M. scrofulaceum |
| Myco 11 (15) | ACA ACA GCT CTG GC | M. szulgai |
| Myco 12 (16) | TGA TTT CCC TCG CCG | M. vaccae |
| Myco 13 (17) | GCG GTT ACT GCC TGC TG | M. xenopi |
| Myco 14 (18) | GAA ACC CCC AAG G | M. terae |
| Myco 15 (19) | TTC CTC AAA GCA GTG | M. flavescens |
| Myco 16 (20) | CAG TCC ATC GAA ACA | M. smegmatis |
| Myco 17 (21) | CAC GCG GAC TGG CC | M. malmoense |
| Myco 18 (22) | ACC ACT TCA ACC GA | M. simiae |
| Myco 19 (23) | TCC CGA AAC CAA CA | M. marinum-ulcerance |
| Myco 20 (24) | CAA CAC TCT TGG ACG | M. gastri |
| Myco 21 (25) | CAC GGA CGG ACC | M. avium |
| Myco 22 (26) | ACA CGG ATC GAC C | M. intracellulae |
| Myco 23 (27) | CAC GTC GAC CTC AG | M. genavense |
| Myco 24 (28) | CAC GTC GAC CAA A | M. lentiflavum |

*Nucleotide sequence of PNA probe was expressed by DNA sequence.

EXAMPLE 4

Fabrication of PNA Chips

1) To fabricate PNA oligonucleotide chips, epoxy group-containing allyl glycidyl ether (AGE) was covalently bound to polystyrene plastic substrates to obtain epoxy plastic slides. 100 pmole of each of amino group-containing PNA probes and an equal amount of spotting buffer (3×SSC, 0.01% SDS) were thoroughly mixed and spotted on the epoxy plastic slides using a piezorray microarraying system (Perkin Elmer, America) according to a probe array pattern shown in FIG. 4. The resultant plastic slides were left in a temperature and humidity-adjustable chamber at 60° C. under a humidity condition of 70% for 16 hours.

2) The plastic slides were dipped in a 50 mM Tris-HCl(50° C., pH9.0) solution for 30 minutes, washed with 0.2% SDS (×2, for 2 minutes) and then with distilled water (×2, for 2 minutes), centrifuged at 1,000 rpm for 5 minutes, and dried. Thus-completed PNA oligonucleotide chips were stored at room temperature in a dark room until use.

EXAMPLE 5

Determination of Genotypes of Mycobacterial Species

1) Rhomadine- or biotin-labeled PCR products were mixed with a hybridization solution (3×SSC, 0.001% SDS) in a mixture ratio of 1 to 20. In the case of using biotin-labeled PCR products for fluorescent reaction, 1 ug/ml of streptavidin-cyanine 3 was added to the resultant mixed solution.

2) 90 μl of the mixed solution was supplied to a plastic slide-containing chamber via an inlet of the chamber and incubated at 55° C. for 30-60 minutes.

3) The chamber was washed with 1×SSC at room temperature for 5 minutes and then with 0.1×SSC for 2 minutes, and dried at room temperature.

4) Result Assay

Figure 5:
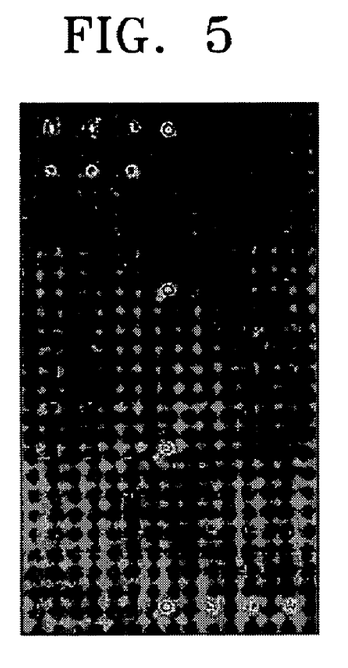
FIG. 5 is a fluorescent image showing the detection results of PCR-amplified products of *Mycobacterium tuberculosis*, which is a species of tuberculosis *mycobacteria*, using a PNA chip according to the present invention.
Figure 6:
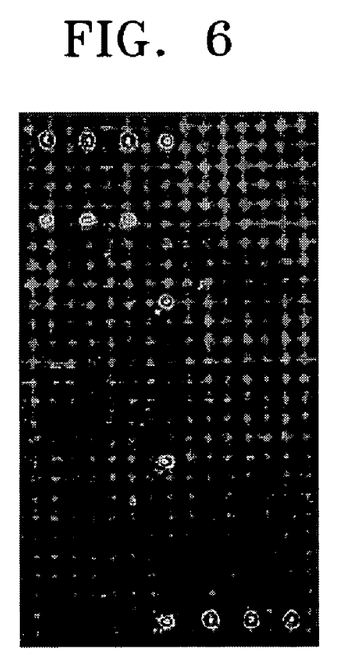
FIG. 6 is a fluorescent image showing the detection results of PCR-amplified products of *M. avium-intracellulare*, which is a species of nontuberculosis *mycobacteria*, using a PNA chip according to the present invention.
Figure 7:
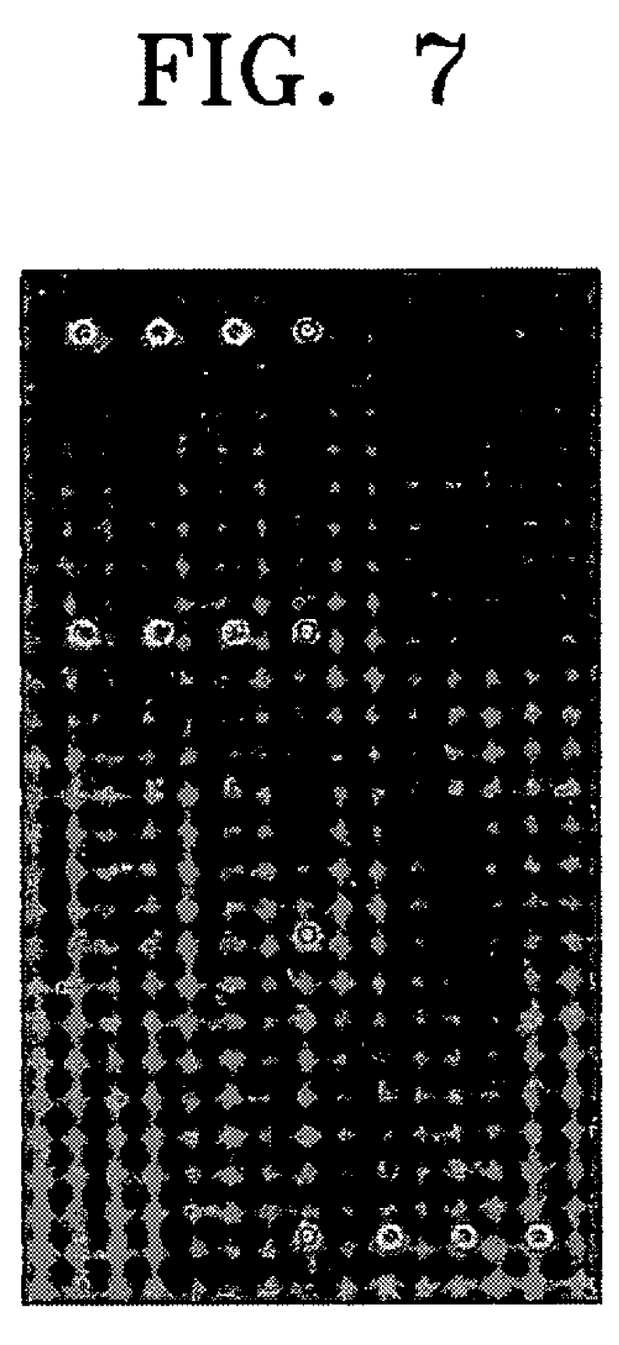
FIG. 7 is a fluorescent image showing the detection results of PCR-amplified products of *M. chelonae*, which is a species of nontuberculosis *mycobacteria*, using a PNA chip according to the present invention.

Fluorescent signals were detected using a scanner (GenePiX4000B, Axon instruments, America), and the genotypes of mycobacterial species were determined using a typing program developed by the present inventors. Examples of detection of fluorescent signals are shown in FIGS. 5 through 7. FIG. 5 is a fluorescent image showing the detection results of PCR-amplified products of *Mycobacterium tuberculosis* and FIG. 6 is a fluorescent image showing the detection results of PCR-amplified products of *M. avium-intracellulare,* which is a species of nontuberculosis *mycobacteria.* FIG. 7 is a fluorescent image showing the detection results of PCR-amplified products of *M. chelonae.*

As described above, according to a PNA chip and a method of determining the genotypes of mycobacterial species using the PNA chip of the present invention, the genotypes of mycobacterial species which are causes of tuberculosis and respiratory diseases can be determined within a short term with good sensitivity and specificity. Therefore, detection of the presence of mycobacterial species in test samples, and after confirmation of the presence of mycobacterial species, identification of the mycobacterial species and determination of whether or not the mycobacterial species are tuberculosis-causing mycobacterial species can be achieved promptly and accurately.

What is claimed is:

1. A peptide nucleic acid (PNA) chip for determining the genotypes of mycobacterial species wherein a plurality of probe PNAs is immobilized on a plastic substrate coated with an epoxy group-containing polymer,
    wherein the plurality of probe PNAs comprises
    a probe PNA consisting of SEQ ID NO: 5,
    a probe PNA consisting of SEQ ID NO: 6, and
    a probe PNA consisting of a sequence selected from the group consisting of SEQ ID NOs: 7-28,
    wherein each probe PNA is immobilized in an individual spot; and
    wherein the mycobacterial species are selected from the group consisting of *M. tuberculosis* complex, MAC complex, *M. fortuitum, M. chelonae, M. abscessus, M. kansasii, M. gordonae, M. scrofulaceum, M. szulgai, M. vaccae, M. xenopi, M. terrae, M. flavescens, M. smegmatis, M. malmoense, M. simiae, M. marinum*-ulcerance, *M. gastri, M. avium, M. intracellulae, M. genavense,* and *M. lentiflavum.*

2. The PNA chip of claim 1, wherein the plastic substrate is a transparent plastic substrate made of a material selected from the group consisting of polymethylmethacrylate (PMMA), polycarbonate (PC), polynorbonene, cyclic olefin copolymer (COC), fluorinated polyimide, polystyrene (PS), styrene-butadiene copolymer (SBC), acrylonitrile butadiene styrene (ABS), styrene acrylonitrile (SAN), and polysulfone.

3. The PNA chip of claim 1, wherein the epoxy group-containing polymer is a copolymer of an epoxy group-containing acrylate monomer and an epoxy group-free acrylate monomer.

4. The PNA chip of claim 3, wherein the epoxy group-containing polymer is a copolymer of an epoxy group-containing acrylate monomer and a highly viscous acrylate monomer, as represented by Formula 1 below:

$$-[CR^3R^3-CR^1R^3-X]_n-, \quad (1)$$

wherein $R^1$ is an epoxy-containing ester, $R^3$ is hydrogen or an alkyl group, and X is a highly viscous acrylate compound.

5. The PNA chip of claim 4, wherein the highly viscous acrylate monomer is selected from the group consisting of dipentaerythrithol hydroxy pentaacrylate (DPHA), 9-ethyleneglycol diacrylate (9-EGDA), pentaerythritol tri,tetraacrylate (PETA), polyethyleneglycol 400 diacrylate, tripropyleneglycol diacrylate, trimethylol propane triacrylate, and dipentaerythritol hexacrylate.

6. The PNA chip of claim 3, wherein the epoxy group-containing polymer is a copolymer of an epoxy group-containing acrylate monomer and an acrylate derivative capable of adhering to the plastic substrate, as represented by Formula 2 below:

$$-[CR^3R^3-CR^1R^3-CR^3R^3-CR^3R^3]_n-, \quad (2)$$

wherein $R^1$ is an epoxy-containing ester, $R^2$ is an alkylester, and $R^3$ is hydrogen or an alkyl group.

7. The PNA chip of claim 6, wherein the acrylate derivative capable of adhering to the plastic substrate is selected from the group consisting of methylmethacrylate (MMA), ethylacrylate, ethylmethacrylate (EMA), n-propylacrylate, n-propylmethacrylate, isopropylacrylate, and isopropylmethacrylate.

8. The PNA chip of claim 1, wherein the content of the epoxy group in the epoxy group-containing polymer is 20-30%.

9. The PNA chip of claim 1, further comprising an ether-containing or ether-free carboxylic acid linker of 5-8 carbon atoms with an amino functional group that is connected to amino terminals of the probe PNAs.

10. A method of determining the genotypes of mycobacterial species, the method comprising:
    a) applying a reaction sample containing target DNAs to the PNA chip of claim 1;
    b) hybridizing the target DNAs with the plurality of probe PNAs, said target DNAs are labeled with a fluorescent material;
    c) washing the PNA chip to remove a nonspecific reaction product; and
    d) detecting a fluorescent signal emitted from the resultant PNA/DNA hybrids.

11. The method of claim 10, wherein the target DNAs are obtained by PCR amplification using primers having DNA sequences selected from the group consisting of SEQ ID NOs: 1-4.

12. The method of claim 11, wherein the primers are biotin- or rhodamine-labeled primers.

13. The PNA chip of claim 1, wherein the plurality of probe PNAs comprises:
    a probe PNA consisting of SEQ ID NO: 5,
    a probe PNA consisting of SEQ ID NO: 6,
    a probe PNA consisting of SEQ ID NO: 7,
    a probe PNA consisting of SEQ ID NO: 8,
    a probe PNA consisting of SEQ ID NO: 9,
    a probe PNA consisting of SEQ ID NO: 10,
    a probe PNA consisting of SEQ ID NO: 11,
    a probe PNA consisting of SEQ ID NO: 12,
    a probe PNA consisting of SEQ ID NO: 13,
    a probe PNA consisting of SEQ ID NO: 14,
    a probe PNA consisting of SEQ ID NO: 15,
    a probe PNA consisting of SEQ ID NO: 16,
    a probe PNA consisting of SEQ ID NO: 17,
    a probe PNA consisting of SEQ ID NO: 18,
    a probe PNA consisting of SEQ ID NO: 19,
    a probe PNA consisting of SEQ ID NO: 20,
    a probe PNA consisting of SEQ ID NO: 21,
    a probe PNA consisting of SEQ ID NO: 22,
    a probe PNA consisting of SEQ ID NO: 23,
    a probe PNA consisting of SEQ ID NO: 24,
    a probe PNA consisting of SEQ ID NO: 25,
    a probe PNA consisting of SEQ ID NO: 26,
    a probe PNA consisting of SEQ ID NO: 27, and
    a probe PNA consisting of SEQ ID NO: 28.

* * * * *

```
SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
cccgaagccr gtggcctaac c                                             21

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
ccaaggcatc caccatgcgc cc                                            22

<210> SEQ ID NO 3
<211> LENGTH: 17
<212> TYPE: DNA
<213> ORGANISM: Artificial Sequence
<220> FEATURE:
<223> OTHER INFORMATION: primer

<400> SEQUENCE: 3
ctttctaagg agcacca                                                  17
```

```
<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
gatgctcgca accacta                                                    17

<210> SEQ ID NO 5
<211> LENGTH: 14
<212> TYPE: DNA
<213> ORGANISM: Artificial Sequence
<220> FEATURE:
<223> OTHER INFORMATION: probe

<400> SEQUENCE: 5
aaacaccaca cccc                                                       14

<210> SEQ ID NO 6
<211> LENGTH: 14
<212> TYPE: DNA
<213> ORGANISM: Artificial Sequence
<220> FEATURE:
<223> OTHER INFORMATION: probe

<400> SEQUENCE: 6
aaacactgga cccc                                                       14

<210> SEQ ID NO 7
<211> LENGTH: 14
<212> TYPE: DNA
<213> ORGANISM: Artificial Sequence
<220> FEATURE:
<223> OTHER INFORMATION: probe

<400> SEQUENCE: 7
cacctggaac aagt                                                       14

<210> SEQ ID NO 8
<211> LENGTH: 15
<212> TYPE: DNA
<213> ORGANISM: Artificial Sequence
<220> FEATURE:
<223> OTHER INFORMATION: probe

<400> SEQUENCE: 8
gaccgagtgt tgtct                                                      15

<210> SEQ ID NO 9
<211> LENGTH: 12
<212> TYPE: DNA
<213> ORGANISM: Artificial Sequence
<220> FEATURE:
<223> OTHER INFORMATION: probe

<400> SEQUENCE: 9
cacccgcaac cg                                                         12

<210> SEQ ID NO 10
<211> LENGTH: 14
<212> TYPE: DNA
<213> ORGANISM: Artificial Sequence
<220> FEATURE:
<223> OTHER INFORMATION: probe
```

```
<400> SEQUENCE: 10
agcgagtaac cact                                                         14

<210> SEQ ID NO 11
<211> LENGTH: 16
<212> TYPE: DNA
<213> ORGANISM: Artificial Sequence
<220> FEATURE:
<223> OTHER INFORMATION: probe

<400> SEQUENCE: 11
ccactacaga tgccta                                                       16

<210> SEQ ID NO 12
<211> LENGTH: 15
<212> TYPE: DNA
<213> ORGANISM: Artificial Sequence
<220> FEATURE:
<223> OTHER INFORMATION: probe

<400> SEQUENCE: 12
cacttgttgg gatgc                                                        15

<210> SEQ ID NO 13
<211> LENGTH: 12
<212> TYPE: DNA
<213> ORGANISM: Artificial Sequence
<220> FEATURE:
<223> OTHER INFORMATION: probe

<400> SEQUENCE: 13
gacagcaccc ga                                                           12

<210> SEQ ID NO 14
<211> LENGTH: 14
<212> TYPE: DNA
<213> ORGANISM: Artificial Sequence
<220> FEATURE:
<223> OTHER INFORMATION: probe

<400> SEQUENCE: 14
accactcaga acga                                                         14

<210> SEQ ID NO 15
<211> LENGTH: 14
<212> TYPE: DNA
<213> ORGANISM: Artificial Sequence
<220> FEATURE:
<223> OTHER INFORMATION: probe

<400> SEQUENCE: 15
acaacagctc tggc                                                         14

<210> SEQ ID NO 16
<211> LENGTH: 15
<212> TYPE: DNA
<213> ORGANISM: Artificial Sequence
<220> FEATURE:
<223> OTHER INFORMATION: probe

<400> SEQUENCE: 16
tgatttccct cgccg                                                        15

<210> SEQ ID NO 17
```

```
<211> LENGTH: 17
<212> TYPE: DNA
<213> ORGANISM: Artificial Sequence
<220> FEATURE:
<223> OTHER INFORMATION: probe

<400> SEQUENCE: 17
gcggttactg cctgctg                                                17

<210> SEQ ID NO 18
<211> LENGTH: 13
<212> TYPE: DNA
<213> ORGANISM: Artificial Sequence
<220> FEATURE:
<223> OTHER INFORMATION: probe

<400> SEQUENCE: 18
gaaaccccca agg                                                    13

<210> SEQ ID NO 19
<211> LENGTH: 15
<212> TYPE: DNA
<213> ORGANISM: Artificial Sequence
<220> FEATURE:
<223> OTHER INFORMATION: probe

<400> SEQUENCE: 19
ttcctcaaag cagtg                                                  15

<210> SEQ ID NO 20
<211> LENGTH: 15
<212> TYPE: DNA
<213> ORGANISM: Artificial Sequence
<220> FEATURE:
<223> OTHER INFORMATION: probe

<400> SEQUENCE: 20
cagtccatcg aaaca                                                  15

<210> SEQ ID NO 21
<211> LENGTH: 14
<212> TYPE: DNA
<213> ORGANISM: Artificial Sequence
<220> FEATURE:
<223> OTHER INFORMATION: probe

<400> SEQUENCE: 21
cacgcggact ggcc                                                   14

<210> SEQ ID NO 22
<211> LENGTH: 14
<212> TYPE: DNA
<213> ORGANISM: Artificial Sequence
<220> FEATURE:
<223> OTHER INFORMATION: probe

<400> SEQUENCE: 22
accacttcaa ccga                                                   14

<210> SEQ ID NO 23
<211> LENGTH: 14
<212> TYPE: DNA
<213> ORGANISM: Artificial Sequence
<220> FEATURE:
<223> OTHER INFORMATION: probe

<400> SEQUENCE: 23
```
tcccgaaacc aaca                                                14

<210> SEQ ID NO 24
<211> LENGTH: 15
<212> TYPE: DNA
<213> ORGANISM: Artificial Sequence
<220> FEATURE:
<223> OTHER INFORMATION: probe

<400> SEQUENCE: 24
caacactctt ggacg                                               15

<210> SEQ ID NO 25
<211> LENGTH: 12
<212> TYPE: DNA
<213> ORGANISM: Artificial Sequence
<220> FEATURE:
<223> OTHER INFORMATION: probe

<400> SEQUENCE: 25
cacggacgga cc                                                  12

<210> SEQ ID NO 26
<211> LENGTH: 13
<212> TYPE: DNA
<213> ORGANISM: Artificial Sequence
<220> FEATURE:
<223> OTHER INFORMATION: probe

<400> SEQUENCE: 26
acacggatcg acc                                                 13

<210> SEQ ID NO 27
<211> LENGTH: 14
<212> TYPE: DNA
<213> ORGANISM: Artificial Sequence
<220> FEATURE:
<223> OTHER INFORMATION: probe

<400> SEQUENCE: 27
cacgtcgacc tcag                                                14

<210> SEQ ID NO 28
<211> LENGTH: 13
<212> TYPE: DNA
<213> ORGANISM: Artificial Sequence
<220> FEATURE:
<223> OTHER INFORMATION: probe

<400> SEQUENCE: 28
cacgtcgacc aaa                                                 13